United States Patent [19]

Wen et al.

[11] Patent Number: 5,054,496
[45] Date of Patent: Oct. 8, 1991

[54] METHOD AND APPARATUS FOR RECORDING AND ANALYZING BODY SURFACE ELECTROCARDIOGRAPHIC PEAK MAPS

[75] Inventors: Yingmei Wen; Zhengping Wang; Xiaojie Liu; Yuping Zhang; Qiding Fang; Xiaoyin Wang; Chun Shen, all of Beijing, China

[73] Assignee: China-Japan Friendship Hospital, Beijing, China

[21] Appl. No.: 379,608

[22] Filed: Jul. 13, 1989

[30] Foreign Application Priority Data

Jul. 15, 1988 [CN] China .................................. 88208287
Dec. 30, 1988 [CN] China .................................. 88108998

[51] Int. Cl.$^5$ ............................................. A61B 5/04
[52] U.S. Cl. ..................................... 128/696; 128/699; 128/802; 128/639
[58] Field of Search ............... 128/696, 699, 639, 802, 128/695; 364/413.06

[56] References Cited

U.S. PATENT DOCUMENTS

| | | | |
|---|---|---|---|
| 4,573,474 | 3/1986 | Scibetta | 128/696 |
| 4,608,987 | 9/1986 | Mills | 128/639 |
| 4,700,712 | 10/1987 | Schmid | 128/699 |
| 4,729,377 | 3/1988 | Granek et al. | 128/802 |
| 4,812,976 | 3/1989 | Lundy | 364/413.06 |

OTHER PUBLICATIONS

Chung, E. K. (1985), Electrocardiography: Practical Application . . . , ISBM 0-8385-2167-3, pp. 1-4.
Klinge, R. (1988), The Electrocardiogram: An Illustrated Manual, ISBN 0-89838-938-6, pp. 21-27.
Mirvis, D. M. (Ed) (1988), Body Surface Electrocardiographic . . . , ISBN 0-89838-983-6, pp. 21-27, 43-62.
Dam, RTh van and Oosterom A van (Eds) Electrocardiographic body . . . , ISBN 0-89838-834-1, pp. 31-38, 39-48.
Igarashi, A et al. (1987) Determinatino of the Site of . . . , Jpn Heart J 28(2):165-76.
Ikeda, K. et al. (1987), Temporal Changes in Body Surface Peak . . . , J Electrocardiol 20(3):212-8.
Cooksey, J. D. et al, (1977) Clinical Vectorcardiography . . . , ISBN 0-8151-1851-1, pp. 32-35.
Microwave Shielding Material Factory Jia Xing, Zhejiang Province, People's Republic of China, Inventor: Prof. Lin, Yi Fan.
Cooksey, J. D. et al. (1977), Clinical Vectorcardiography . . . , ISBN 0-8151-1851-1, pp. 120-121.

Primary Examiner—Francis Jaworski
Assistant Examiner—George Manuel
Attorney, Agent, or Firm—Majestic, Parsons, Siebert & Hsue

[57] ABSTRACT

The peak potential values of each cardioelectric wave components detected from the body surface are uniquely presented as a few iso-potential and isochronous contour maps by the electrocardiac peak mapping (EPM) method and apparatus described. The change in the size and the contour of the relevant EPM maps provides a simple, non-invasive, yet sensitive means for clinical diagnosis of at least the following heart diseases:

1) the locations and sizes of myocardial infarction (hereafter, MI),
2) primary and second cardiomyopathies,
3) locations and sizes of "non-Q-wave MI", which can not be diagnosed by conventional electrocardiography, and
4) various intracardiac conduction blocks and Wolff-Parkinson-White syndrome,
5) various repolarization abnormalities and their quantitative analysis.

The EPM apparatus comprises an elastic Waistcoat with embodied special electrodes, signal preprocessors, a multiplexer, a main differential amplifier, and a general purpose computer with appropriate software. The EPM analysis includes the identification of the peak potential and peak time displacement, the contruction of the isopotential and isochronous maps and the diagnosis of heart diseases. The diagnosis is achieved by comparison of the statistically obtained normal values to that of a patient. The complete EPM process can be carried out within ten minutes.

12 Claims, 8 Drawing Sheets

METHOD AND APPARATUS FOR RECORDING AND ANALYZING BODY SURFACE ELECTROCARDIOGRAPHIC PEAK MAPS

TECHNICAL FIELD

This invention relates to non-invasive electrocardiographic recording, automated analysis and diagnosis techniques. In particular, EPM proposes a novel method for recording and analyzing body surface electrocardiographic peak data. The method and apparatus can be used to diagnose heart diseases. Hereafter, we will use the following definition of "apparatus": it is used to represent equipment, components, parts, and physical objects in general. "Method" is defined as the processing and transfer of information. The "processors" and medium of transfer for information can be either machine or human. Information, in our case, refers to analog and digital body surface electrocardiographic signals, contour maps, and medical knowledge.

BACKGROUND OF THE INVENTION

Conventional 12-lead Electrocardiography

It is known that the use of electrocardiography for detecting electrophysiological changes in the heart is the simplest and the most effective non-invasive diagnostic method at present (See refs. 1 and 2). Hereafter, ECG would represent current conventional 12-lead electrocardiography. Electrocardiograms from ECG are effective in the diagnosis of MI of anterior-septal, anterior, inferior, and lateral ventricular walls. However, the sensitivity is about 50-70%. Furthermore, because it can not determine the size of infarction, many difficult and complicated cases can not be definitely diagnosed. In addition, because the quantity of information from the scattered 12-lead electrodes is smaller and non-uniform, false negative diagnosis are inevitable and the seriousness of a patient's condition can not be estimated from the size of pathological changes in ECG.

The theoretical foundation of the 12-lead ECG and its method of diagnosis is built upon the mono-equivalent dipole theory, in which the heart is considered as a small dipole at the center of an infinitely sized sphere of homogeneous conductor. During a cardiac cycle, countless dipoles generated by the electrocardiac changes are simplified into a series of instantaneous resultant vectors with respect to a fixed point. Due to the limited amount of information provided by the 12-lead ECG, this simplifying assumption is required for the construction of the electrophysiological model of the heart. However, this assumption is far from the actuality, because:

1) the human body is not spherical,
2) the conductivity of different parts of human body tissue is nonhomogeneous,
3) the heart is located at one side of the human body, and
4) the relative volume of human body to the heart is not infinite.

Although many electrocardiographic phenomena can be explained by this theory, some electrocardiographic phenomena of ECG can not be explained. Thus the electrocardiography is unsatisfactory in clinical applications.

Examples of Other Surface Electrocardiographic Methods

A. Synchronous Isopotential Mapping

The body surface multi-lead instantaneous synchronous isopotential mapping (hereafter SIM) is an "advanced" non-invasive electrocardiographic diagnostic method relative to ECG (refs. 3 and 4). The theoretical foundation of SIM is the multi-dipole theory which assumes that the cardiac depolarization is composed of multiple depolarization fronts in different directions at any instance in time. The abnormal dipoles generated by electrocardiac events of local myocardium are relatively independent but all correspond to local regions on the body surface. Data from SIM, when interpreted by this theory, has advanced electrocardiographic diagnosis by providing results which coincided better with actual conditions, thereby increases the sensitivity of electrocardiographic diagnosis.

The SIM apparatus comprises of up to 200 electrodes placed over the chest and back. The body electrocardiographic potential values are taken at many predetermined time points (instantaneous) of the cardiac cycle, usually in milliseconds intervals. Tens, up to hundreds, of isopotential maps displaying the instant electric potentials of the heart are generated during each cardiac cycle. The analysis of SIM is made by examination of many consecutive maps to detect changes, if any, in cardioelectric potentials. Therefore, SIM can improve the sensitivity of electrocardiographic diagnosis; but the cognitive signal detection problem makes it difficult for doctors to find the proper signal (pathological changes) buried in the noise (insignificant normal patterns) and to use SIM data to form a mental configuration of a complete cardiac cycle. Furthermore, since SIM requires instantaneous measurements, multiplexing of leads to channels (preamp, amplifier, and filter) required by high conformity (gain) and synchronization (time) makes SIM apparatus large and difficult to transport. The tuning and adjusting of the multiple channels and placement of electrodes are also very tedious and cumbersome.

B. Body Surface Isointegral Mapping

Body surface iso-integral maps is another electrographic method (ref.5). It condenses both time and voltage into maps of integrals at multiple surface lead points. For example, the QRST isointegral map would have contours for the area (voltage X time) under the QRST curves of each point in the body surface. However, any changes in contours of such maps may be caused by either voltage or time changes. This condensation loses important information obtainable from time or voltage alone. Furthermore, the placement of electrode leads is as difficult as SIM.

C. Body Surface Isochronic Map

Body surface isochronic R map constructed from SIM data has also been reported (ref. 6). These isochronic maps involve QR time (ventricular activation time) which is from the starting point of QRS complex of ECG to the different R peaks. This interval differs in various portions of the heart and among different individuals. Therefore, the method can not represent properly about the speed of impulse spreading over the ventricular wall from one point to another. Additionally, the problems of adjusting the channels and placing electrode remain the same as SIM.

D. Devices for Sensing Body Surface Electric Signals

Many attempts have been made to develop a simpler, yet more sensitive and reliable method for detecting body surface cardioelectric signals. In U.S. Pat. No. 4,763,660, an elastic vest with electrodes has been used to reduce the labor required in applying electrodes onto the body surface and increase the sensitivity of signal detection.

SUMMARY OF THE INVENTION

Development of EPM

Differing from the existing SIM apparatus which displays instant value of the cardioelectric wave potentials, electrocardiac peak mapping (EPM) utilizes the peak value of the cardioelectric wave components for presentation, comparison and diagnosis of heart conditions. These cardioelectric wave components are the P, Q, R, S, T, etc. waves defined by conventional ECG. The EPM isopotential map is composed of peak voltages of each ECG wave component measured at body surface electrode points. The lines in the contour graph represent the same voltage, hence the name "isopotential". Similarly, the isochronous map is composed of the time displacement of each ECG peak waves occurred with respect to a fixed reference point in a cardiac cycle. The lines in the graph represent the same time, hence the name "isochronous". The resultant maps are named P, Q, etc. isopotential or isochronous maps respectively. Since each cardioelectric wave components represent a particular activity of the heart, any changes in size and contour of isopotential and/or isochronous maps provide pathognomonic criteria for quantitative analysis and diagnosis of heart diseases.

Importance of EPM

The invention of EPM method is based on the condensation of the major cardiac information into a few contour maps distinct from any other existing body surface maps. The importance of displaying and analysis of cardioelectric peak potential values is as follows:

1) cardioelectric peak potentials are the most informative parameters in characterizing electrophysiological voltage changes of the heart;
2) peak potential values of each cardioelectric wave components and their displacements measured on body surface form distinct contours which can be used for differentiation and diagnosis of heart diseases;
3) EPM isopotential map provides a direct correlation between areas of electrical activities on the myocardial walls and areas of electrocardiographic signals on the body surface;
4) EPM isochronous maps provide a direct measurement for the depolarization and repolarization condition of the heart;
5) multiple-lead measurement of electrocardiac activities by EPM widens the information obtainable from conventional ECG and enables more specific anatomical diagnosis.

Advantage of EPM

The main advantage of EPM is to provide a simple, direct and sensitive means to determine the presence, location, and size of myocardial infarction (hereafter MI) and the presence of cardiomyopathies as well as intracardiac conduction defects. This advantage also permits the demonstration that the clinically diagnosed "non-Q-wave MI" has no theoretical basis; because most clinical "non-Q-wave MI" actually has pathological Q waves located at the body surface regions undetectable by conventional 12-lead ECG. In contrast, EPM has also shown that many of the so called "non-specific" ST-T changes, as used in current medical terminology, do have distinguishable characteristics under EPM as different clinical disorders, such as coronary heart disease, primary cardiomyopathies, diabetic cardiomyopathy and others.

Compared to SIM, the EPM analysis has the following advantages:

1) reduce information overload by going from 10's or 100's of SIM contours to generally 5 or 6 EPM maps (in some cases, a finer resolution of more than 6 maps will be needed), while capturing most of the clinically significant SIM data;
2) enhance signal to noise ratio in detecting pathological changes because of distinct, either positive or negative and diagnostic patterns;
3) provide time parameters to indicate the speed and direction of heart excitation during cardiac depolarization and repolarization;
4) provide direct correlation between areas of electrical activities originated from the myocardial walls and areas of electrocardiographic signals covered by the body surface leads;
5) in conjunction with the EPM apparatus, simplify the application of leads and tuning and adjustment of electrode channels.

Objectives of EPM

The invention is to provide the EPM apparatus and EPM method for performing the following:

1) detecting and organizing high quality electrocardiographic information over the body surface via a non-invasive method,
2) building of simple but comprehensive peak isopotential, isochronous, and their combined maps from such data for easy recognition and analysis,
3) deriving contour parametric values for quantitation.

The maps are then used to infer electrocardiographic changes and diagnose heart diseases.

Additional objectives achieved by the invention are:

4) generate highly reliable and consistent data of electrophysiological changes in the heart,
5) provide a simple, portable, low-cost, easy-to-use apparatus,
6) achieve automatic diagnostic capability for heart diseases, in particular, MI, cardiomyopathies, and conduction defects, through quantitative analysis of the contour distributions,
7) provide fine detail information about the heart abnormalities, such as the size of MI, degree of conduction blocks in myocardial depolarization and repolarization, and
8) provide conventional 12-lead ECG information -- -EPM can be used as a conventional ECG.

Objectives #1, #4, #5, and #8 are achieved by the EPM apparatus. Objectives #2, #3, #5, #6, and #7 are achieved by the EPM method.

Description of the EPM Method

The information collected by EPM method is based on a regular array of points located around the chest. The array forms a roughly rectangular tiling of the approximate elliptical cylinder that is the surface of the body. The reference line is the right midaxillary line. The voltage and time measurements at each point over a complete cardiac cycle form a complete data set which is then processed as follows:

1) identification of peaks, both positive and negative and any possible subpeaks (local maxima and minima when voltage is plotted against time), for each point,
2) determination of voltage and time of each P, Q, R, S, +T, and −T (and r' and s' if present) wave peaks derived from (1),
3) construction of contour maps from description (2), in which the contours are either isopotential or isochronous lines,
4) identification of maxima and minima of contours from (3), such as R-centers, Q-centers, multiple centers, etc.,
5) determination of gradient (slope) values of the region around the local maxima and minima (4), such as R-notches, etc.,
6) determination of the area covered by boundaries of contour peaks and valleys, as derived from the maxima and minima information (4), and
7) deviation of values of (4)-(6) in patients from normal data constructed from group mean value ±2 standard deviation of corresponding maps,
8) automatic diagnosis.

Objective #2 is achieved from (3). Objective #3 is achieved with the quantitation of contour data as provided by (4)-(7). Expert systems (computer or/and human) can now be used for the determination of normal and abnormal conditions. If abnormal, the derived data (4)-(7) can also provide sufficient information to make further determination of the clinical cause, which achieves Objective #6. The few maps that are constructed from (3) can be easily read by physicians (or computer) to determine clinical diseases and their scope which achieves Objective #7. Finally, because the arrangement of the points in plane is a superset of the points in the 12-lead ECG, Objective #8 is achieved from the raw data as it is sent to (1).

Description of the EPM Apparatus

Figure 3:
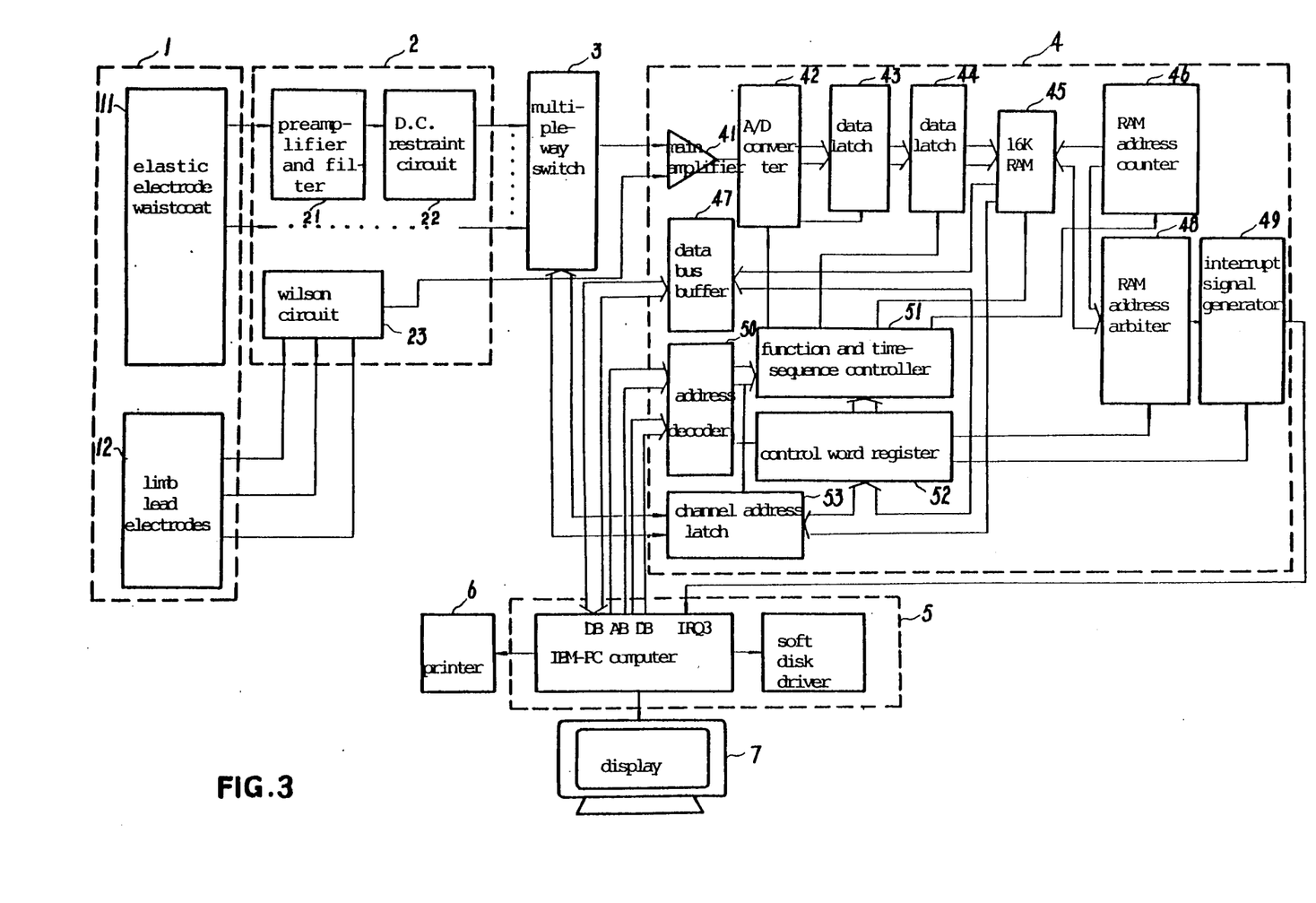
FIG. 3 is a block diagram of the system of an apparatus to illustrate the preferred embodiment of the EPM apparatus of this invention.

In the preferred embodiment, the EPM apparatus is composed of the following components (FIG. 3):

1) an elastic waistcoat (thoracic corset) with embedded soft electrodes,
2) Wilson unipolar limb lead system as voltage references,
3) signal preprocessor including multiple body surface electrocardiographic channels and a Wilson circuit,
4) multiplexer from the preprocessor (3) to the acquisition unit (5),
5) high speed data acquisition unit composed of a main amplifier, an A/D converter, two data latches, random access memory, a RAM address counter, a data bus buffer, an address arbiter, an interrupt signal generator, an address decoder, a function and time-sequence controller, a control-word register, and a channel address latch,
6) computer with the software to perform the EPM method, and
7) display and printer to the computer.

The electrodes on the waistcoat are designed as snap-on buttons and wrapped by electrically conducting cloth. The base of the electrodes, with their lead wires, are sewn into predetermined locations on the elastic coat. The limb leads provide the voltage signals for the Wilson circuit (ref. 7), which generates the reference potential for the electrodes on the waistcoat. The preprocessor contains a preamp and a filter for each incoming signal from the waistcoat electrodes. There is a DC restraint circuit after the filter stage to minimize DC interference and maintain constant DC potential across all channels without external regulation or adjustment.

Electrocardiographic signals flows from the preprocessor to the multiplexer and then out to the acquisition unit. The multiplexer is a n-to-1 switch where n matches the number of channels in the preprocessor. Switching takes place at predetermined time intervals governed by the function and time-sequence controller in the acquisition unit. Since DC potential conformity is provided at the output of the preprocessor, the multiplexer eliminates the would-be replication of many components and circuitry in the acquisition unit. The justification for the multiplexer is because EPM is particularly interested in the peak voltage or peak time, it is not necessary to acquire data at extremely high time resolutions. Therefore, as a cost-saving design consideration, with concomitant reliability improvement, EPM uses a multiplexer at this point in the signal processing flow. An added benefit is the singular main amplifier in the acquisition unit which eliminates the need for separate adjustment and tuning required to achieve proper consistency among different electrodes. This results in considerable savings in the cost and complexity of EPM apparatus as compared to prior systems, such as SIM. Furthermore, the reduction of complicity increases reliability and performance.

The acquisition unit uses the reference voltage provided by the Wilson circuit and the output of the multiplexer to determine the actual potential of the electrocardiographic event. The electrocardiographic voltage is sampled by the A/D converter and stored into RAM until accessed by the computer. After which, the computer can process the values, via the EPM method, to derive the results needed.

The unique property of the waistcoat of this invention is the application of an electrically conducting fabric (Ref. 7) as conducting material of the electrodes and the selection of foam as part of the bases of the electrodes which ensures the maximum contact between electrodes and the body surface.

Objective #1 is achieved by combination of the waistcoat (1), and the preprocessor (3). Objective #4 is achieved by (1), Wilson unipolar lead system (2), and (3). Objective #5 is achieved by the multiplexer (4) and the acquisition unit (5).

DETAILED DESCRIPTION OF OPERATIONAL SPECIFICATION

Arrangement of Electrode leads

Figure 1:
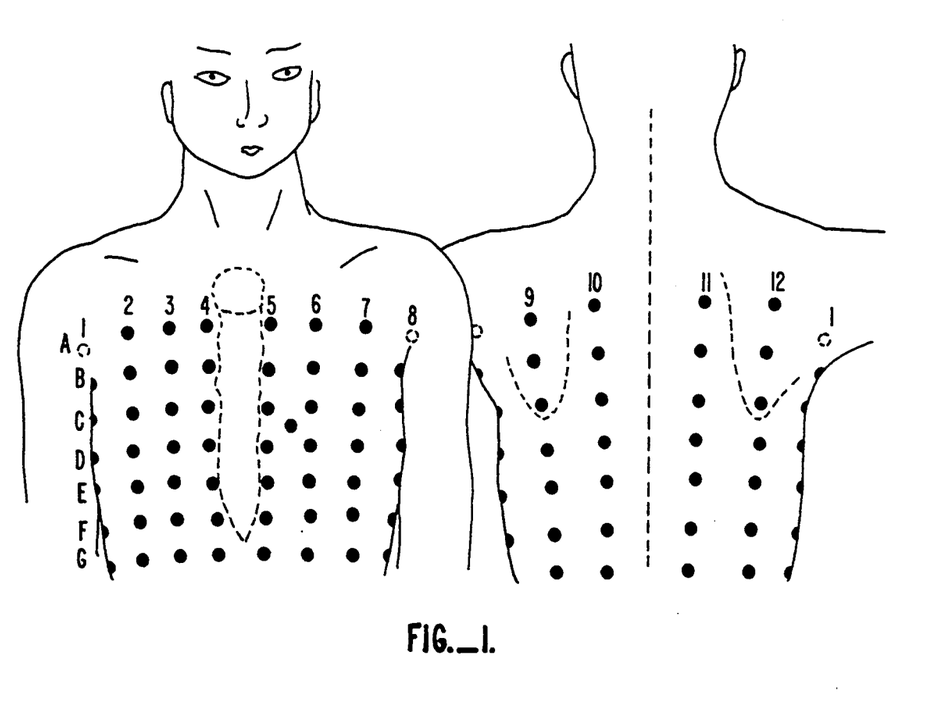
FIG. 1 is a schematic view which shows the locations of the 85-lead electrodes on the complete trunk of the human body in the preferred embodiment of the invention.

FIG. 1 shows the location of the 85 leads on the waistcoat as they make contact with the human body (the number of leads used in this example is flexible, since the button bases can be sewn at will into a number of different configurations). The corresponding site on the waistcoat are the predetermined location where the electrodes are sewn. Fifty-six electrodes are arranged into 7 rows (A to G) and 8 (1 to 8) columns on the anterior surface of the chest. An additional electrode is placed at the V3 position of conventional ECG midway between C5 and D6. This lead is placed in order to obtain the complete 12-lead ECG data. Twenty-eight electrodes arranged into 7 rows (A to G) and 4 columns (9 to 12) are distributed over the posterior region of the thoracic region. The 85 (56+1+28) electrodes forms the square tiling on the body surface with the right mid-axillary line as demarcation reference line.

Waistcoat

The schematic drawing of the waistcoat and the snap-on button electrodes are illustrated in FIGS. 2A-2F. The coat (FIGS. 2A and 2B) is elastic, soft, comfortable and portable. It conforms with the patient's chest wall, which allows proper contact for measuring body surface voltages. The electrodes is about 2-3mm thick. It is foam based and wrapped by electric-conducting fabric (Ref. 7). This fabric is soft and light weight. It is cotton based and plated with electrically conducting metallic compounds. Special treatment allowed the fabric to have low resistance and good conductivity. The snap-on portion of the electrodes can be easily removed for sterilization and recycling without losing their electric sensitivity. The wires for the electrodes are neatly routed within the coat. All these contribute to make EPM easy to use in a clinical setting as compared to many existing cardioelectric surface mapping systems.

FIG. 2C-2F show the detailed structure and organization of the electrode used in EPM. The letters in the figures refer to the following:
a) electric waist coat,
b) electrodes,
c) electric wires,
d) plug,
e) cover of the waist coat,
f) snap button,
g) conducting cloth, and
h) foam.

Figure 2A:
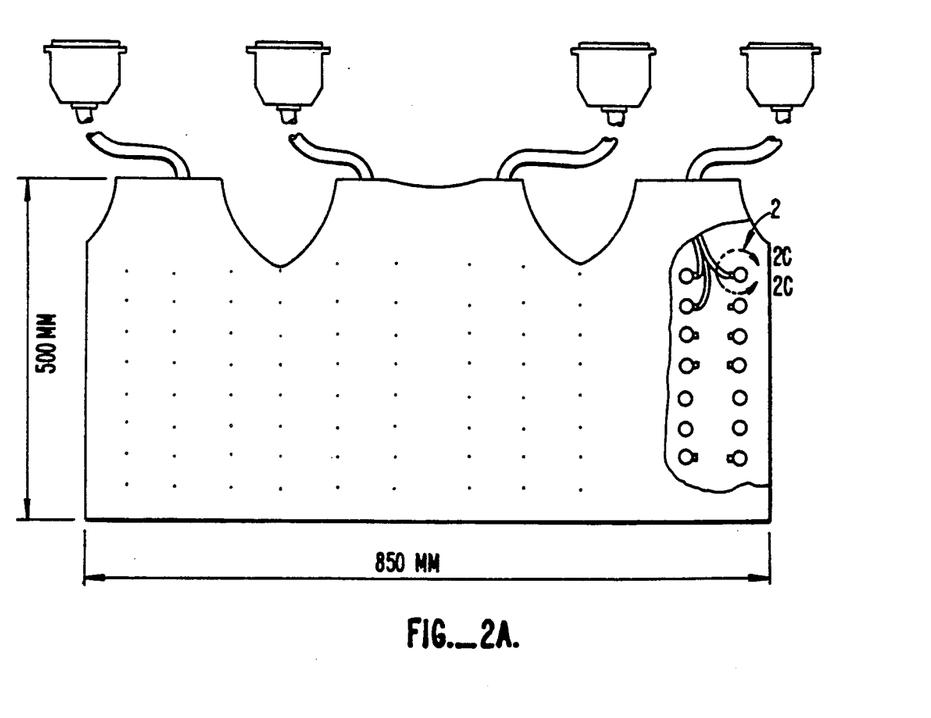
FIG. 2A is an external view of a waistcoat with a portion of its outside cover removed to show the electrodes, for illustrating the preferred embodiment.
Figure 2B:
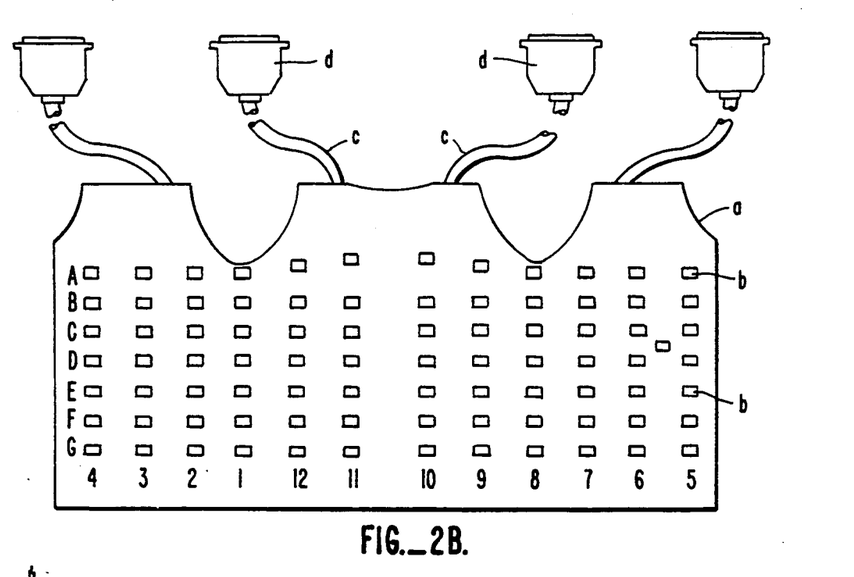
FIG. 2B is an internal view of the waistcoat shown in FIG. 2A to illustrate the lay out of the electrodes.
Figure 2C:
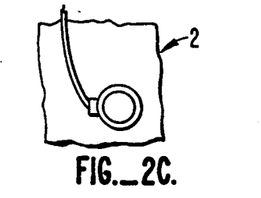
FIG. 2C is an enlarged view of circle 2C in FIG. 2A.
Figure 2D:
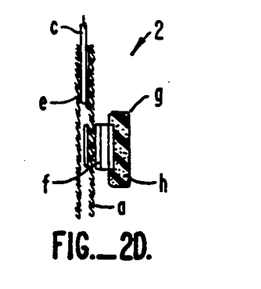
FIG. 2D is a side view of a single electrode-button of the waistcoat shown in FIG. 2A.
Figure 2E:
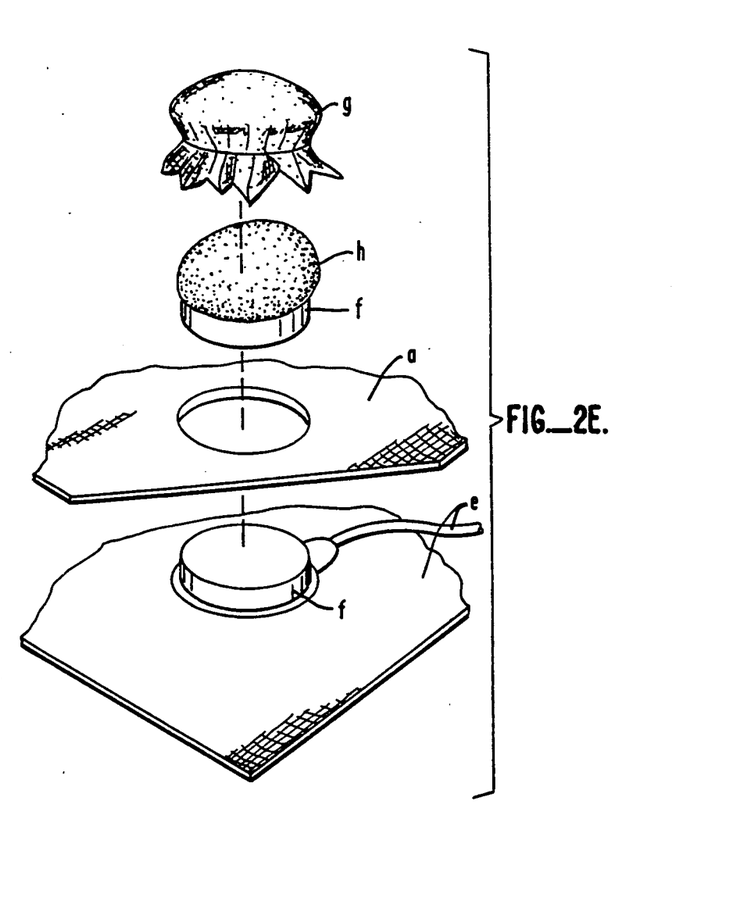
FIG. 2E is an enlarged side view of a single electrode button of the waistcoat shown in FIG. 2A which illustrates in more detail the structure of the electrode-button.
Figure 2F:
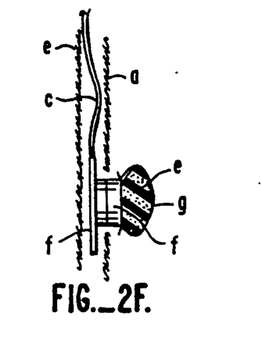
FIG. 2F is an exploded view of the electrode-button of FIG. 2E to illustrate the invention.

As shown in FIGS. 2E, 2F, the button that acts as the electrode comprises a first base portion comprising a button top and a button base which can be snap fit into each other through a hole in the inner fabric (a) of the coat. The button also comprises an elastic soft portion (h) which may simply be made of foam. The button also comprises a third portion made of the conductive fabric described above and in reference 8. The conductive fabric is secured to the button (f) by any suitable means such as by tying with a thread and is therefore also electrically connected to the button. Thus, when the three portions of the button are assembled together, the button base will be sandwiched between the inner fabric (a) and the outer fabric (c) of the coat. The button top portion, the foam and the conductive fabric will protrude from the inner surface of the coat and are therefore in position to contact the person's trunk when the person is wearing the coat.

The coat itself may be of a conventional design and comprises an inner elastic fabric (a) and an outer elastic fabric (c). The softness of the conductive fabric and foam and the compressibility of the foam render them suitable cushions to shield the person's skin from the button (f) which may be made of an electrically conductive material such as metal. Such composition of electrode-buttons permit the electrodes to conform to the shape of the person's trunk and achieves better electrical contact. The construction of the button also increases the area of contact with the person's chest to further enhance the accuracy of measurement. Therefore the signals sensed by the electrodes are more reliable and increases the accuracy of the measurement.

Electronic Block Diagram

FIG. 3 shows a block diagram for connecting the various components of the EPM apparatus. The following is the description of the circuit blocks (in dotted lines).

1) waistcoat and electrode leads,
2) preprocessor,
3) multiplexer (85-to-1 multiple-way switch),
4) high speed data acquisition unit,
5) computer with the appropriate EPM software,
6) printer, and
7) display.

A. Electrode leads (1)
  11) elastic waistcoat with embedded electrodes as described above, and
  12) four limb lead electrode system as used in conventional ECG.
B. Preprocessor components (2)
  23) Wilson circuit, and eighty-five channels, each composed of:
  21) preamplifier with a gain of 10 and filter,
  22) DC restrain circuit.

The preprocessor (2) performs a critical function in the conditioning of the raw signal. The body surface electrocardiographic voltage is of millivolt range and the frequency of its main signal components is below 100 Hz, which makes the measurements easily affected by respiration movement and its electromuscular activity. Furthermore, the signal's DC voltage can vary with individuals and even with different locations on the same individual. This DC voltage can often be many times higher than the amplitude of the body surface electrocardiographic voltage. If the DC component is not restrained, then the amplified voltage, after the main amplifier (41), would go beyond the operational scope of the A/D converter (42) which could cause an overranging error and loss of valuable data samples. Accordingly, on each channel, a DC restraint circuit (22) is added after the preamplifier and filter (21). The restraint circuit is typical of a second order highpass filter, e.g. Butterworth. This restraint can effectively restrain the DC voltage but does not influence the effective frequency range of the body surface electrocardiographic signal. The end result is a DC voltage being kept uniform by the reasonable selection of the parameters of the circuits without the need of regulation by a potentiometer.

C. Multiplexer (3)

All signals from the preprocessor are multiplexed into the high speed data acquisition unit (4). The n-to-1 multiplexer (3) is controlled by the sequencer (51). This multiplexer ensures that all body surface electrocardiographic signals are amplified by the same amount, thereby eliminating the need for adjustment of multiple amplifiers.

D. High speed data acquisition unit (4)
  41) main differential amplifier with a gain of 100,
  42) 8-bit A/D converter,
  43) and 44) data latches,
  45) random access memory (hereafter RAM) bank,
  46) RAM address counter,
  47) data bus buffer,
  48) RAM address arbiter,
  49) interrupt signal generator,
  50) address decoder,
  51) function and time sequence controller (hereafter, sequencer),
  52) control word register, and
  53) channel address latch.

The sequencer (51), controlled by the computer (5), determines the stages of processing of the signal in the acquisition unit (4). The address decoder (50) latches a control word from the computer into the control word register (52). The function performed depends on the value of the control word. At the beginning of the data gathering, the number of data points to convert is loaded into the acquisition unit by the address decoder into the sequencer.

Data Acquisition Unit in Acquisition Mode

If the control word is "WRITE", the acquisition unit is placed in data acquisition mode. In this mode, the acquisition unit is a two-stage pipeline processor. The first stage is the A/D conversion and the second stage is the storage of the digitalized signal value.

The first stage starts as the channel address latch (53) is loaded with a channel address from the computer by using the same address decoder and is sent out to the multiplexer. The selected signal is sent to the positive input of the differential main amplifier (41) and the reference voltage from the Wilson circuit (23) is sent to the negative input. The latching of the channel address will cause the sequencer to generate a delayed trigger to the A/D converter. The delay period is based on the multiplexer switching time and stabilization time of the main amplifier. This trigger will start A/D conversion. After 600 nanoseconds, the "end-of-conversion" signal from the A/D will trigger the data latch (43). At this point, the signal's digital value is latched to input of the second data latch (44).

The second stage start at the same time the "start-conversion" trigger is sent to the A/D converter. The sequencer performs the following sequence in this stage:
  A) the address counter (46) is incremented by 1,
  B) the second data latch (44) is triggered, and
  C) the value of the second data latch is stored in the RAM bank(45) at the address specified by the counter (46).

Therefore, while performing the A/D conversion on the current channel, the value of the previous channel is stored in the RAM bank. Every new channel address sent by the computer will cause this pipeline mechanism to step through to the next stage. When the number of converted data is equal to the pre-set value, the RAM address arbiter (48) triggers the interrupt signal generator (49), which sends an interrupt request signal to the computer. As the computer respond to this interrupt, it will enter an interrupt service program to read the data.

Data Acquisition Unit in Read Mode

When the control word is set as "READ", the acquisition unit will provide the data stored in the RAM bank to the computer. After the address decoder is stored by an input instruction, the sequencer will:
  A) increment the RAM address counter by 1,
  B) read the content in RAM bank addressed by the counter,
  C) the value is then sent to the data bus buffer (47), and
  D) read by the computer throuqh a data bus.

Data Acquisition Unit Timing Characteristics

In order to retain synchronicity at a high resolution, a scan cycle is performed once every 2 milliseconds. The time needed to actually complete the scan of 85 leads using this acquisition unit requires only several hundred microseconds. Therefore, it has ample margin of tolerance.

DETAILED DESCRIPTION OF PROCESSING SPECIFICATION

This is a detailed description of the EPM method, i.e. the processing of data after it is received by the computer. The EPM method includes the following steps:
  1) data preprocessing,
  2) peak identification,
  3) calculation of the voltage of the peaks,
  4) calculation of the time displacement of voltage peaks with respect to the reference Frank vector,
  5) construction of peak isopotential and isochronous contour maps,
  6) derivation of parametric values of the contours, and
  7) analysis for heart diseases.

Data Preprocess

The preprocessing is performed on all channels individually. The data for preprocessing is the raw digitalized values from the acquisition unit. After preprocessing, the data can be stored on a disk for later retrieval. The preprocessing consists of the following steps.

1) The electrocardiographic data of several cardiac cycles are averaged in order to reduce the random noise and raise the signal to noise ratio.
2) The averaged data are digitally filtered by a comb-filter to reduce the AC power line frequency interference, i.e. the 50 Hz or 60 Hz hum of the AC power lines, while preserving as much as possible, the useful components of the data. The features desirable of this filter are simple structure, high operating speed, good filtering effect, and sufficient for this invention.
3) The baseline for the electrocardiographic data signal is regulated. Because the baseline is easily influenced by low frequency noise, such as breathing, and floating effects, the baseline fluctuations must be eliminated. The conventional ECG controls this by a potentiometer. In EPM, the adjustment is made by software. A horizontal reference line is derived for a series of sample measurements. Then, the deviation of the sample from the reference line is used as the actual signal.
4) Remove other interfering signals through preprocessing software.
5) If data points are lost, interpolated data can be inserted to restore consistency.
6) The presence of irregular beats (premature or delayed contractions) are excluded from the averaging by the preprocessing program.
7) Beat of particular interest (e.g. the premature ventricular beat), are selected and processed separately as needed.

Peak Identification

The data from preprocessing is used to derive a modified Frank vector (ref. 9). The Frank vector (F) is a mono-pole resultant vector representing the cardioelectric activity of a complete cardiac cycle. It is used in EPM to establish a fixed and absolute time frame for cardiac landmarks. Within this time frame, a window corresponding to the landmarks, e.g. P, Q, R, S, or T electrocardiographic waves, can be scanned for the peak values in each channel. F is calculated from the sum of three axis vectors. The X-axis vector is represented by the values at C1 and C8, Y-axis vector is A5 and F7, and Z-axis vector is C5 and C10 (the positions refer to FIG. 1). Note that this modified Frank system is based on Cartesian coordinates, with a skewed Y-axis which follows the axis of the heart. Since F is a resultant vector, the electrocardiographic activities detected by the body surface leads are contained within the scope of F, i.e. the time of the QRS complex of any lead will fall within the time period of F's QRS complex.

Calculation of Peak Time and Voltage

The starting point of the ventricular depolarization wave in the heart corresponds to the starting point of the QRS complex on F. Thus, this marks the beginning of the time window where values are to be scanned. The end of the window corresponds to the time when F leaves the QRS complex. As in ECG, the maximal voltage value in this window is identified as the R peak which subsequently partition the window into two subwindows. The minimal voltage value in the pre-R subwindow is the Q peak, and the minimal voltage value in the post-R subwindow is the S peak. Similarly, P wave window and T wave window are derived. Both +P peak (maximum) and −P peak (minimum) can be obtained and so are +T and −T peaks which occurs after the QRS complex.

The window, determined from F, is also used as the absolute reference time point for measuring the time displacement of individual peaks, i.e. the peak's latency relative to the beginning of each window (subwindow).

Construction of Maps

From the above extraction, every measured point on the body surface will have a particular peak potential and time value for each wave of interest. When the body surface is unrolled into a plane, the peak potential values become the height values, thus forming a 3-D bar graph. Since continuity is assumed, a contour map can be graphed as isopotential map for the peak voltage measured in every wave at each body surface point. Similarly, a isochronous contour map is generated from the time displacement values of each wave peak.

A combined map overlays the contours of both isopotential and isochronous maps on top of each other for the specific wave of interest. Each contour is graphed with distinct lines, indicated by a number, color or texture. The synergistic usage will be described in section VII below.

Calculation of Parametric Values

The positions of contour maxima and minima are calculated by basic mathematical methods. The gradient around these maxima and minima can also be derived. The contour area covered by an elevation or depression can be obtained heuristically based on rate of change of gradients. Combined contour parameters, such as the number of contour maxima and minima, shape of contour elevations and depressions, time of peak occurrence, speed and direction of displacement of the isochronic lines etc., can also be obtained using standard techniques and computer programs.

Analysis of Maps

Because of the correlation between myocardial wall activity and electrocardiographic signals on the body surface, the contour maps can be quantified and used to provide diagnostic information. The positions of the electrodes serves as a reference grid which captures the main regions of activities during a cardiac cycle, e.g. P, Q, R, S, and T waves. Any changes in the above calculated values can be used to develop quantitative patterns which subsequently used by expert systems (human and/or computer) via heuristic reasoning, classification algorithms, and other inference engines to perform automatic diagnosis for a wide range of heart diseases as mentioned at the beginning of the introduction.

Conventional techniques may be used to implement the different steps of the method described above taught by this invention.

DESCRIPTION OF EPM MAPS AND EXAMPLES OF THEIR USE IN CLINICAL SETTINGS

Diagnosis of Myocardial Infarction

Figure 4A:
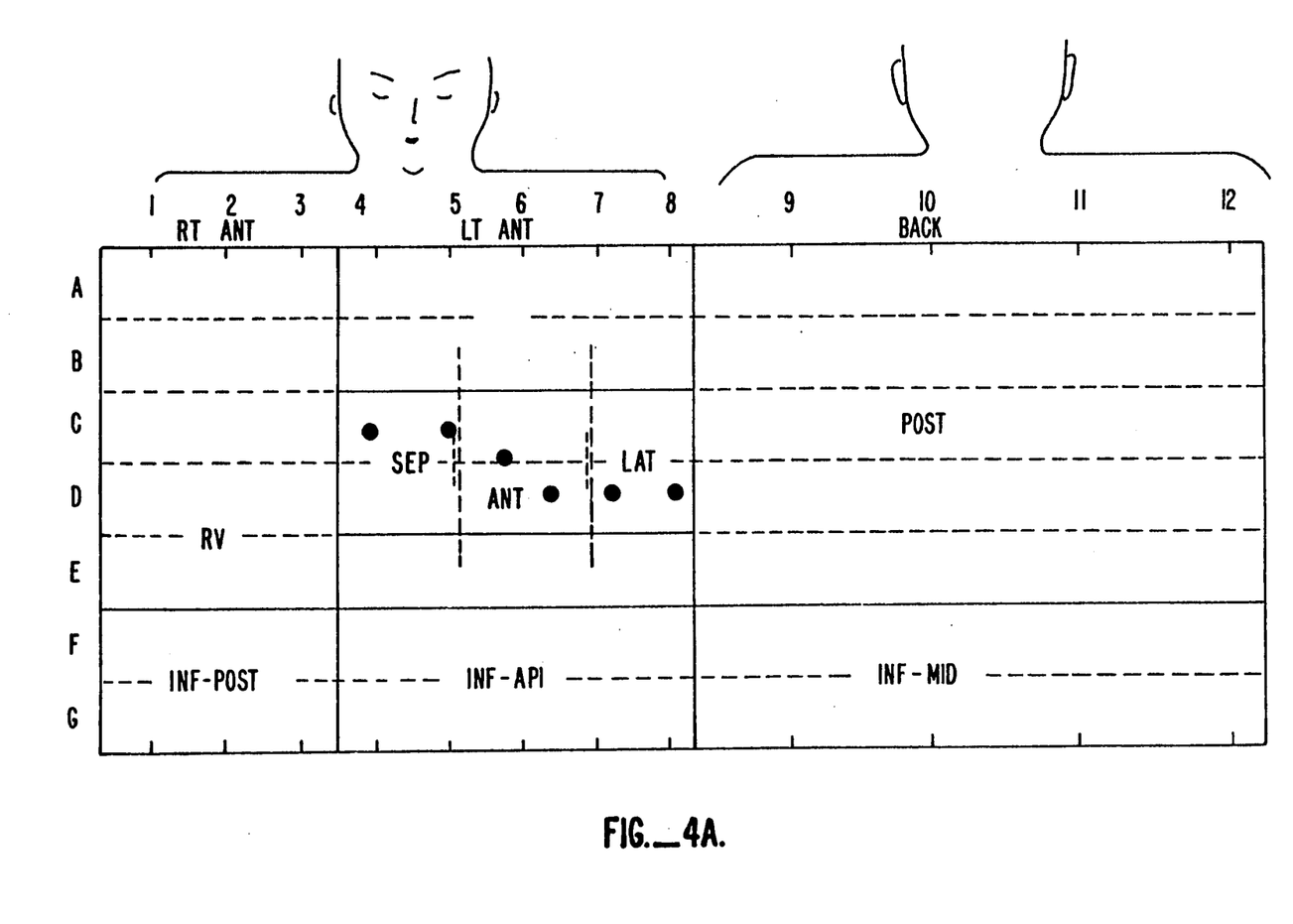
FIG. 4A is a graphical illustration which shows the projection of the cardioelectric activity of the ventricular walls onto the body surface, where the illustration employs the same reference coordinates (A-G, 1-12) as the waistcoat and electrodes in FIGS. 1, 2A-2B.
Figure 4B:
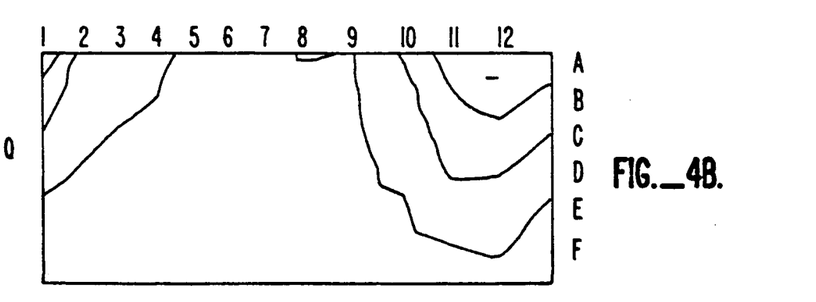
FIGS. 4B-E are graphical illustrations show the contrast of Q and R maps between the normal person and one with diffuse anterior MI.
Figure 4C:
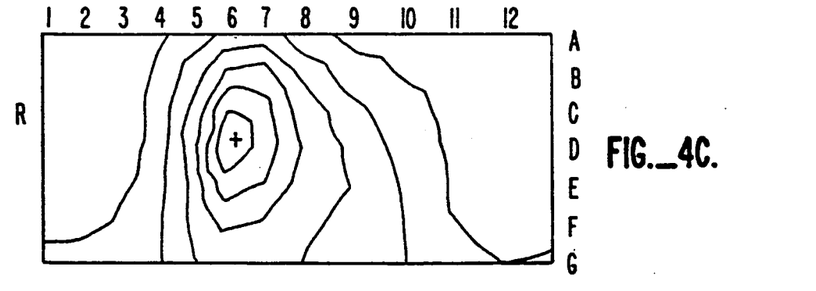

The EPM diagnosis for the location of the myocardial infarction can be tentatively determined as shown in FIG. 4A. The figure shows the correlation of electric activities of the cardiac walls with the body surface electrodes. These correlations have been supported by independent clinical diagnoses and confirmed by animal experiments. The position of each electrode shown in FIGS. 1, 2A, 2B on the body surface can be directly located from FIG. 4A as A to G and 1 to 9. All other legends indicate portions of heart ventricular wall. RT-ANT: right-anterior; LT-ANT: left-anterior; RV: right ventricle; INF-POST: inferior-posterior; INF-API: inferior apical; POST: posterior; INF-MID: inferior-middle; SEP: septal; ANT: anterior, and LAT: lateral.

Figure 4D:
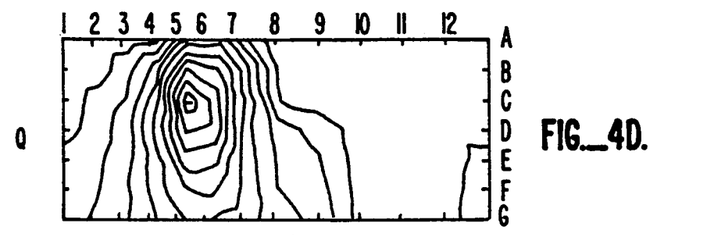
Figure 4E:
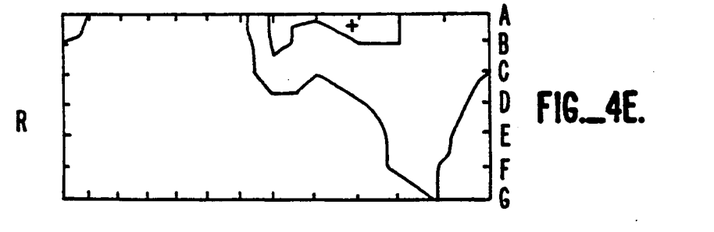

FIG. 4B–4E show the contrast of the Q and R isopotential maps between a normal person (FIGS. 4B and 4C) and one with extensive anterior myocardial infarction (FIGS. 4D and 4E). Under normal conditions, the Q map has a distribution mainly over the front and the back of the upper right chest, and always has a low center (valley) around the coordinates A12 and A1, with a gradual ascending gradient. However, the abnormal Q potential is distributed extensively over the front chest with significant central depression. The gradient (slope) of this valley is also much higher than the gradient in the normal map. Accordingly, while the normal R map is distributed mainly over the left front chest with a large and dome-like elevation center at D6 and C6 coordinates in >90% of the population, the abnormal R map shows that the center of the elevation has moved to the back. The dome-shape of the R map is also deformed with low potential value. These readily noticeable EPM changes are the characteristics of an extensive anterior MI.

Diagnosis of Non-Q-wave Myocardial Infarction

Figure 5A:
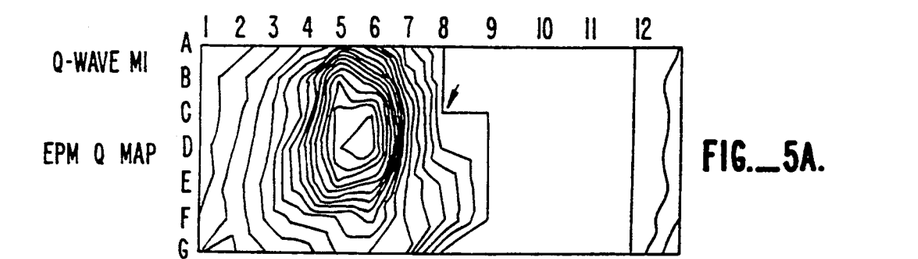
FIGS. 5A, 5C are graphical illustrations which show the contrast of the distribution of EPM Q maps between a case of Q-wave and one with "non-Q wave" MI.
Figure 5B:
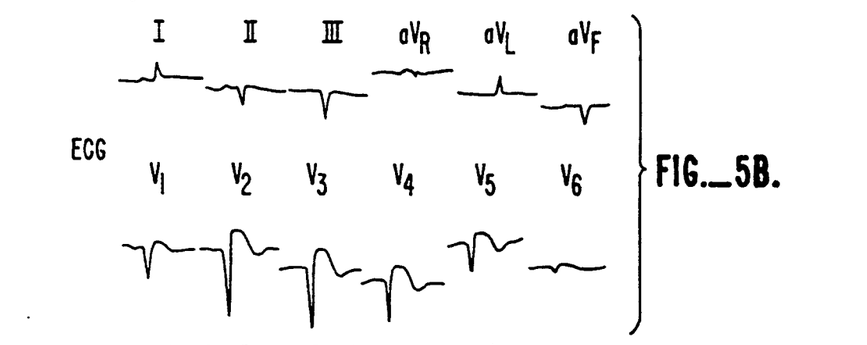
FIGS. 5B, 5D are the corresponding 12-lead ECGs of the cases shown in FIGS. 5A and 5C.
Figure 5C:
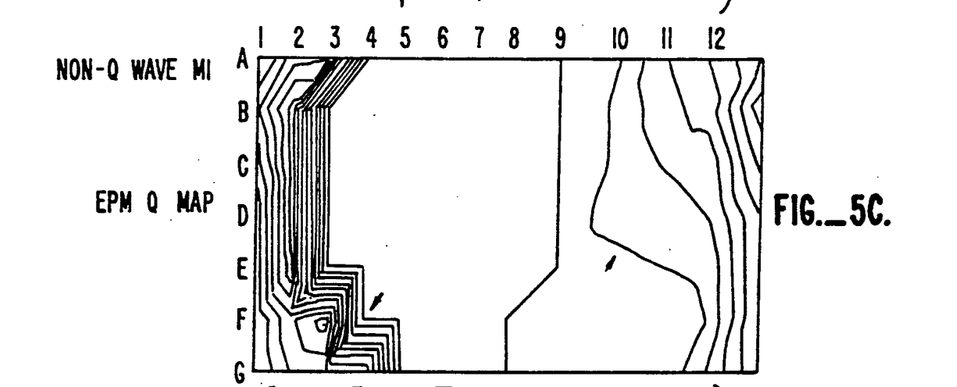
Figure 5D:
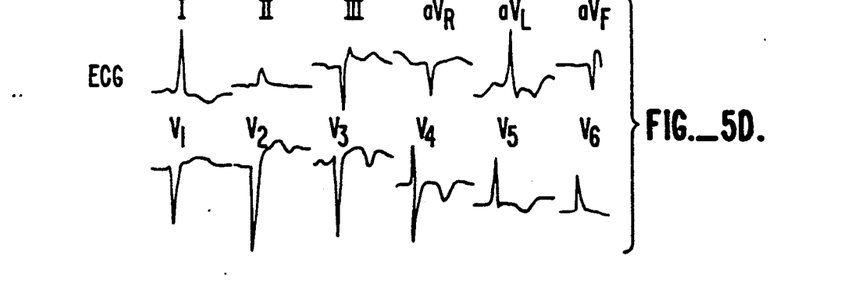

The contrast of the abnormal Q map distribution between a Q-wave MI and a so called "non-Q wave" MI is shown in FIG. 5A and 5C respectively. Current medical practice divides MI into the Q-wave MI and non-Q wave MI according to, electrocardiographically, whether the initial portion of the QRS complex is or is not distorted (with or without abnormal Q wave). This is, in part, because conventional 12-lead ECG can not reveal properly and completely about the cardioelectric activities existed in areas all over the body surface. In contrast, EPM can disclose much wider scope of cardiac activities. In FIG. 5A, one can appreciate that a Q-wave MI patient had an abnormal Q map present over the left precordial chest area which is covered by the precordial chest leads of the conventional 12-lead ECG. Therefore, the abnormal Q potential were detected from V1 to V6 leads of 12-lead ECG as shown in FIG. 5B. In "non-Q wave" MI (FIG. 5C), however, the abnormal Q map (shown in arrows) was located over right lower chest and the lower back (represent infero-posterior MI); these areas are located beyond the scope of conventional 12-lead ECG and therefore escaped from its detection (FIG. 5D).

Diagnosis of Cardiomyopathy

Figure 6A:
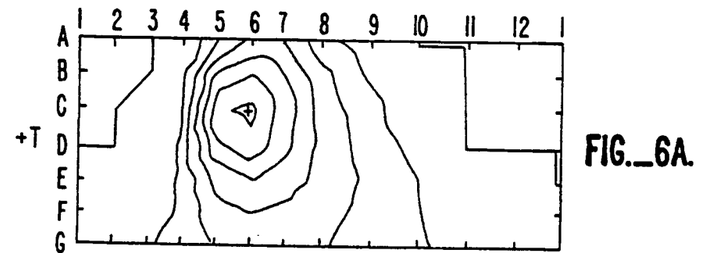
FIGS. 6A-6D are graphical illustrations which show the contrast of the +T and -T isopotential maps between normal and the clinically "non-specific ST-T" changes of cardiomyopathy.
Figure 6B:
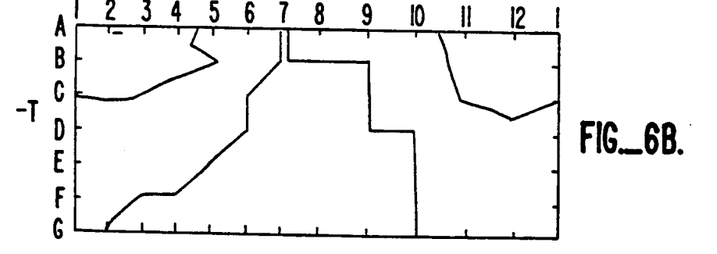
Figure 6C:
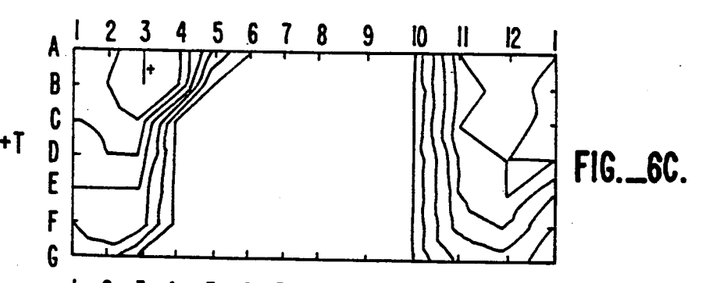
Figure 6D:
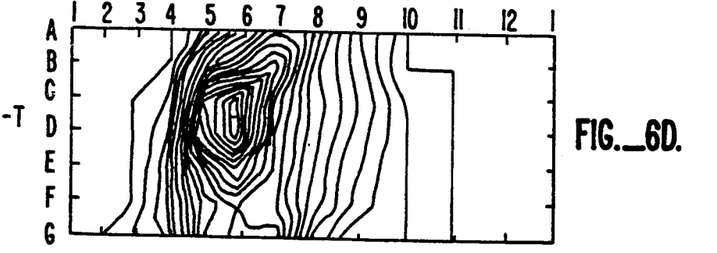

FIGS. 6A–6D show the contrast of +T and −T isopotential maps between a normal person and one with the clinically "non-specific" ST-T changes of cardiomyopathy. The normal person had the +T map located mainly over left chest and −T map over right chest both anteriorly and posteriorly (FIGS. 6A and 6B). The patient of a hypertrophic cardiomyopathy showed a transposition of +T and -T maps indicating a reversed direction of repolarization (FIGS. 6C and 6D). The voltages (shown in compact isopotential lines) of the −T map was significantly increased.

The construction and analysis of the T maps provide new parameters for studying the ventricular repolarization process which are different in many categories of heart diseases. This is achieved either through analysis of it's geographical distribution or it's potential gradients or to both. All these parameters are not obtainable from conventional 12-lead ECG because only the local T wave changes were seen and the changes were non-specific for diagnosis of various diseases. The above changes are also not readily detectable by the SIM because of its large amount of instantaneous dynamic diagrams which can not provide stationary pattern for recognition nor comparison.

Diagnosis of Myocardial Infarction with Cardinal Transduction Block

Figure 7A:
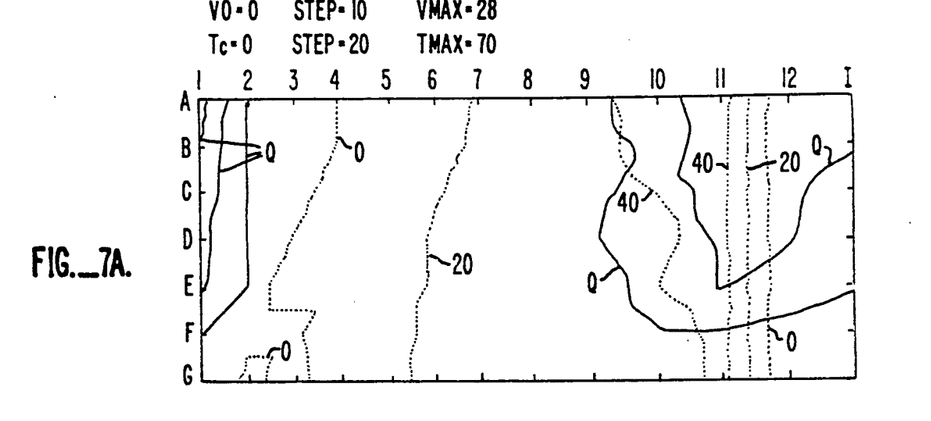
FIG. 7A, 7B are graphical illustrations showing the contrast of a combined isopotential and isochronic map between normal and inferior myocardial infraction.
Figure 7B:
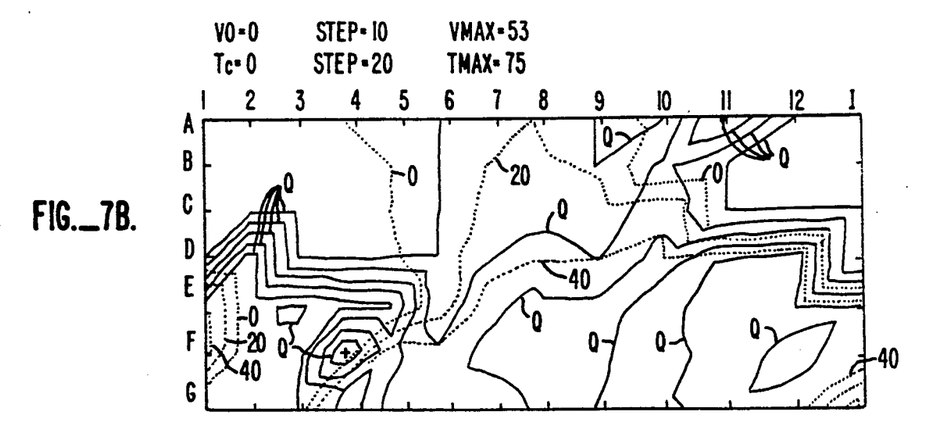

FIG. 7A and 7B show the contrast of a combined isochronic R map on top of isopotential Q map between a normal person and one case of an inferior myocardial infarction respectively. The solid lines Q form the isopotential Q map. The differentially numbered dotted lines form the isochronic R map. Each step in the contour is 20 milliseconds apart (the steps can be changed when desired). In other words, the earliest group of R peaks are labelled "0", and the next group of R peaks "20" and so on. In normal person (FIG. 7A), the Q isopotential map is distributed mainly over the front and the back of the upper right chest; the R isochronic map has its isochronic lines proceed from right anterior to the left and back in a rather parallel fashion. In the patient (FIG. 7B), the center of the Q isopetential map resides at the whole lower chest indicating the presents of an inferior MI; the R isochronic lines are compacted and lying transversely around the ectopic isopotential Q center, suggesting a deteriorated conducting speed and abnormal direction of heart depolarization around the MI area. These combined maps enable a clinician to obtain not only the diagnosis of MI, but also its prognosis through the size of MI and the severity of conduction abnormality.

CONCLUSION

The electrocardiographic peak mapping described here provided a simple, economic, non-invasive, yet comprehensive method for sensitive and reliable electrocardiac analysis of heart diseases. The invention utilizes peak values of cardioelectric ECG wave components as determinants and organizes them into isopotential or isochronic contour maps for presenting, comparison and diagnosis of heart conditions. It condenses the major cardiac information into few contour maps distinct from any instantaneous SIM maps. It can be used for various types of heart abnormalities, in particular, the size and location of myocardial infarction, cardiomyopathies, and the degree of conduction blocks during myocardial depolarization and repolarization.

It is understandable that after reading the description of the above invention, a skilled person in the field can make variations and modifications of the invention. These include, but not limited to, the number and placement of electrodes, types of connections between electrodes and acquisition unit, number of signal channels, number of components and devices, type of computing facility, or programs for data processing. However, these variations and modifications are not incompatible with the spirit of the invention, nor go beyond its scope. Thus, the variations should be included within the extent of the patent protection asked for in the appended claims.

What is claimed is:

1. A body surface electrocardiographic mapping apparatus comprising:

means for continually detecting electrocardiographic signals at n selected points on the surface of a person's chest to provide signals in n channels, n being a positive integer, each channel containing signals detected at a selected point on the person's chest; and means for identifying, mapping the maxima and minima of the signals with respect to a predetermined reference point in time and processing said maxima and minima, wherein said identifying, mapping and processing means also comprises means for correlating the maxima or minima of the signals detected at said n selected points.

2. The apparatus of claim 1, further comprising multiplexer means for multiplexing the n channels of signals into one channel, and wherein the identifying and processing means identifies and processes the maxima and minima of the multiplexed signals.

3. The apparatus of claim 1, wherein said detecting means includes different electrodes placed at said n selected points, and wherein said identifying and processing means includes a single main amplifier for amplifying the multiplexed signals from the different electrodes.

4. A body surface electrocardiographic mapping method comprising:

continually detecting electrocardiographic signals at n selected points on the surface 8 a person's chest to provide signals in n channels, n being a positive integer, each channel containing signals detected at a selected point on the person's chest; and identifying and mapping the maxima and minima of the signals with respect to a predetermined reference point in time, processing said maxima and minima, and correlating said maxima or minima of the signals detected at said n selected points.

5. The method of claim 4, further comprising the step of multiplexing the signals from the n channels into one channel, before the identifying and processing step.

6. A body surface electrocardiographic mapping apparatus comprising:

means adapted for continually detecting electrocardiographic signals at n selected points on the surface of a person's chest to provide signals in n channels, n being a positive integer, each channel containing signals detected at a selected point on the person's chest; and means for processing the signals into isochronous maps and isopotential maps of the n points, wherein the two types of maps are superposed upon one another with respect to the n selected points to facilitate diagnosis.

7. The apparatus of claim 6, said processing means comprising means for identifying the maxima and minima of the signals and for processing said maxima and minima into isopotential and isochronous maps.

8. The apparatus of claim 6, further comprising means for displaying or printing the maps.

9. A waistcoat suitable for use in electrocardiographic mapping comprising:

an elastic coat; and a set of electrodes supported by the coat, said electrodes comprising electrically conductive cloth adapted to contact selected areas of a person's trunk, said cloth comprising a fabric plated with an electrically conducting material, said fabric being soft and adapted to conform to the shape of a person's trunk to increase the areas of contact with the person's trunk, said electrodes having portions that are removable for sterilization and recycling.

10. The waistcoat of claim 9, said person having a heart that emits cardioelectric waves having P, Q, R, S, T components distributed over regions of the person's trunk, wherein said set of electrodes are positioned so that when a person is wearing the waistcoat, said electrodes correspond to the projected positions of the myocardial wall on the body surface of the person and embodies the regions of distribution of the Q, R, S and T maps on the body surface during ventricular depolarization and repolarization and P map during atrial depolarization.

11. The apparatus of claim 9, wherein at least one electrode comprises a button, and a lead or wire wrapped around the button.

12. The apparatus of claim 11, wherein said button comprises:

a first electrically conducting base portion connected to an electrode;

a second top portion made of a soft elastic material;

a third portion comprising a piece of the electrically conductive cloth that covers the second portion, said third portion secured to and in electrical contact with the first portion so that when a person is wearing the coat, the third portion is adapted to contact the person's trunk and supplies electrical signals to the wire or lead, said second and third portions also adapted to act as cushions separating the person's trunk from the first portion to reduce discomfort of the person wearing the coat.

* * * * *